United States Patent
Ishibashi

(10) Patent No.: US 7,917,304 B2
(45) Date of Patent: Mar. 29, 2011

(54) SPOTTER PROVIDED WITH SPOT PATTERN ENCRYPTION FUNCTION AND DETECTION DEVICE COPING WITH SPOT PATTERN ENCRYPTION

(75) Inventor: Tohru Ishibashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 966 days.

(21) Appl. No.: 11/528,603

(22) Filed: Sep. 28, 2006

(65) Prior Publication Data

US 2010/0240122 A1 Sep. 23, 2010

Related U.S. Application Data

(62) Division of application No. 10/868,965, filed on Jun. 17, 2004, now Pat. No. 7,219,019.

(30) Foreign Application Priority Data

Jun. 20, 2003 (JP) ................................. 2003-176548

(51) Int. Cl.
*G06F 19/00* (2006.01)
*G06F 15/00* (2006.01)
*C07H 21/04* (2006.01)

(52) U.S. Cl. ............................... 702/20; 700/1; 536/24.3

(58) Field of Classification Search .......................... None
See application file for complete search history.

(56) References Cited

U.S. PATENT DOCUMENTS

| 5,143,854 A | 9/1992 | Pirrung et al. ............... 436/518 |
| 5,688,642 A | 11/1997 | Chrisey et al. .................... 435/6 |
| 5,908,746 A | 6/1999 | Suzuki et al. ...................... 435/6 |
| 6,017,742 A | 1/2000 | Takenishi et al. ............. 435/180 |
| 6,476,215 B1 | 11/2002 | Okamoto et al. ............ 536/25.3 |
| 2002/0024026 A1* | 2/2002 | Kaushikkar .............. 250/559.06 |
| 2002/0127589 A1 | 9/2002 | Sato et al. ......................... 435/6 |
| 2002/0146715 A1 | 10/2002 | Okamoto et al. .................. 435/6 |
| 2003/0036081 A1* | 2/2003 | Adorjan et al. .................... 435/6 |
| 2003/0059817 A1 | 3/2003 | Okamoto et al. .................. 435/6 |

FOREIGN PATENT DOCUMENTS

| JP | 8-023975 | 1/1996 |
| JP | 8-334509 | 12/1996 |
| JP | 11-187900 | 7/1999 |
| JP | 2001-178442 | 7/2001 |
| JP | 2002-101878 | 4/2002 |
| JP | 2002-267667 | 9/2002 |
| WO | 95/25116 | 9/1995 |

* cited by examiner

*Primary Examiner* — John S Brusca
(74) *Attorney, Agent, or Firm* — Fitzpatrick, Cella, Harper & Scinto

(57) ABSTRACT

Plural probes spotted on a probe immobilization substrate are arranged such that the probes cannot be specified by a third party easily. When the plural probes are spotted on the probe immobilization substrate, a position where each probe is spotted is changed for each probe immobilization substrate to be prepared, whereby types of probes to be arranged in respective spot addresses are encrypted. The preset invention provides a spotter, a dispensing device to be used for the spotter, a probe immobilization substrate that is prepared using the spotter, and a detection device that decodes encrypted positions where the respective probes are spotted.

4 Claims, 4 Drawing Sheets

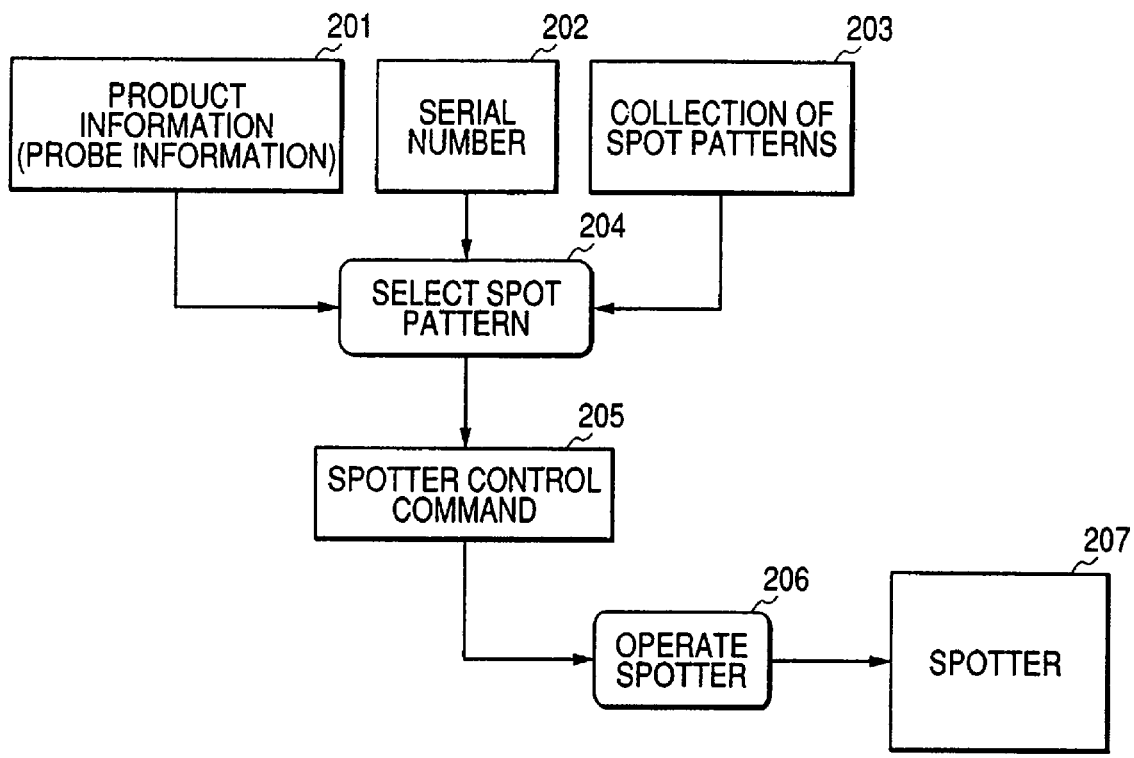
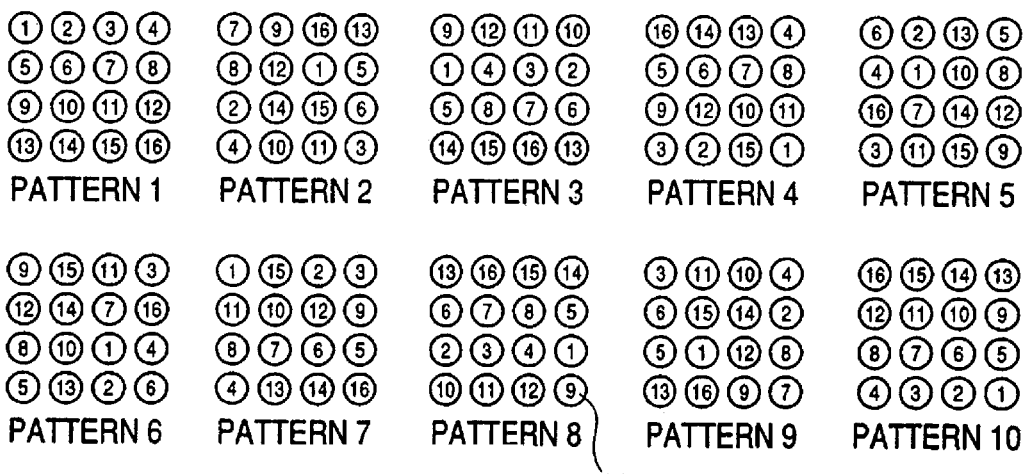

SPOTTER PROVIDED WITH SPOT PATTERN ENCRYPTION FUNCTION AND DETECTION DEVICE COPING WITH SPOT PATTERN ENCRYPTION

This application is a divisional of application Ser. No. 10/868,965, filed Jun. 17, 2004, the contents of which are incorporated by reference herein.

BACKGROUND OF THE INVENTION

1. Field of the Invention

The present invention relates to a spotter that, in a substrate or a solid phase carrier having plural probes capable of specifically binding to a target substance, such as a micro array or a DNA chip, is used for work for immobilizing the plural probes, a detection device for an immobilization substrate on which the plural probes are immobilized, and a dispensing device that dispenses the plural probes to be used by a spotter.

2. Related Background Art

As an example of a probe immobilization substrate that is formed by immobilizing plural probes, which are capable of specifically binding to a target substance, on a surface of a solid phase carrier or a substrate, there is a DNA chip. The DNA chip is a DNA probe array obtained by aligning a large number of DNA fragments or oligonucleotides, which have different base sequences, on a solid phase surface to be immobilized at high density as probes for hybridization reaction. As regards DNA probes to be immobilized on such a DNA chip, combinations of base sequences, which are effective in analyzing expression, mutation, polymorphism, and the like of genes simultaneously, are selected.

As a method of immobilizing nucleic acid molecules on a solid phase surface in array, for example, U.S. Pat. No. 5,688,642 discloses a solid phase oligonucleotide array formed by preparing oligonucleotides in a desired base sequence using photolithography according to solid phase synthesis. On the other hand, WO 95/25116 and U.S. Pat. No. 5,688,642 disclose a preparation method for a solid phase DNA probe array, in which DNA molecules prepared in advance are spotted on a solid phase surface using an ink-jet method.

In addition in a detecting process for a target substance on the basis of probe hybridization reaction, in general, a so-called hybridization reaction is performed in which a target substance labeled by a fluorescent substance or the like is brought into contact with probes of a solid phase probe array to form a specific hybrid between the target substance and the probes. This hybridization reaction is usually a reaction with which the solid phase DNA probe array is brought into contact with or immersed in a solution, in which the target substance is solved, and the target substance forms a specific hybrid with respect to the probes while the target substance and the probes are heated. In this case, conditions for reaction such as concentration and temperature vary depending upon a combination of the probes and the target substance. Moreover, presence or absence of a hybrid formed by allowing the probes and the target substance to bind together, an amount of generation of the hybrid, and the like are observed by detecting fluorescence, which is derived from the fluorescent substance previously used for labeling the target substance, using a detection device such as a fluorescent detector.

As proposed in JP 2002-101878 A, this DNA chip is also used for the gene diagnosis.

A DNA chip for gene diagnosis used actually for diagnosis includes results (information) of observation of presence or absence of a hybrid corresponding to gene information peculiar to each patient, an amount of generation of the hybrid, and the like. For example, in a DNA chip using a fluorescent label, there is no depletion with time of a labeling capability as in a radio element label. Therefore, the DNA chip has an advantage that the results (information) can be read repeatedly. On the other hand, since the results (information) can be read repeatedly, if a name of the patient is leaked together with the DNA chip for gene diagnosis used for diagnosis, even a third party is likely to know a diagnosis result of the patient.

It is needless to mention that, in medical institution, for example, hospitals, measures for confidentiality are taken carefully such that information on individual patients is never leaked to a third party. On the other hand, hospitals and the like often treat instruments and test kits used for diagnosis as medical wastes and entrust disposal thereof to waste disposers having appropriate disposal facilities.

Note that, in a stage of waste disposal entrusted to the waste disposers, naturally, the hospitals are fully equipped with a physical management system meeting standards stipulated for each medical waste, for preventing the outflow and spread of "pathogenic substances", which are likely to adhere to medical wastes. However, in a process of this disposal, although management for "physical leakage" is attained sufficiently, for example, there is a tendency that attention is not sufficiently paid to "information" remaining on a DNA chip used for diagnosis. For example, if a third party can read the "information" remaining on the DNA chip used for diagnosis again under the management for "physical leakage", it is likely that the "information" is leaked to the outside even if the DNA chip itself is not carried out to the outside. Thus, in light of higher confidentiality and management therefor, there is a need for a technique that, even if "information" remaining on a DNA is leaked to the outside, prevents the "information" from being easily linked to diagnostic results of patients.

For example, analysis of base sequences of respective DNA probes constituting a DNA chip is difficult only with an amount of DNAs existing on one DNA chip. However, if respective DNA probes are separated and collected from plural unused DNA chips, and a relatively large quantity of DNAs are obtained, it is possible to analyze base sequences of the DNA probes. That is, when the base sequences of the respective DNA probes constituting the DNA chips are decoded, it is also interpreted what kind of diagnostic result "information" remaining on the DNA chip used for diagnosis is equivalent to. If it is found diagnosis of which patient the DNA chip was used for, as a result, it is possible that a diagnostic result of the patient is leaked to the outside.

Therefore, in light of higher confidentiality and management therefor, there is a need for a technique that, even if plural unused DNA chips could be prepared, can prevent base sequences of respective DNA probes arranged in array on respective DNA chips from being easily analyzed for the DNA chips.

Usually, in a DNA chip for diagnosis used in a medical field, information is disclosed to a user concerning what kind of gene information can be detected by DNA probes constituting the DNA chip. However, since a social position of a source of provision of base sequences of the DNA probes is taken into consideration, the base sequences themselves may be excluded from the information to be disclosed. In addition, when base sequences of DNA probes used in diagnosis are decoded, a problem of maintenance of confidential information also arises, for example, the base sequences are copied by a third party that is not permitted to use the base sequences. From these viewpoints, there is a need for a technique that serves for prevention of decoding such that a third party cannot easily decode base sequences of DNA probes constituting a DNA chip.

SUMMARY OF THE INVENTION

The present invention has been devised in order to solve the above-mentioned problems, and it is an object of the present invention to provide: a technique for, when plural types of probes, which are capable of specifically binding to a target substance, are spotted in predetermined array-like spot positions provided on a surface of a solid phase substrate to manufacture a probe array, applying a random change which cannot be easily recognized, to an arrangement pattern of types of probe molecules, which are spotted in the respective array-like spot positions, for each probe array; a spotter that makes it possible to change spot addresses of the plural kinds of probes based on a spot pattern to which such changing treatment has been applied; a method of detecting target plural kinds of probes, in association with the change of the spot addresses, after decoding the spot positions of the plural kinds of probes, which are spotted based on a spot pattern to which such changing treatment has been applied, based on information to be detected on the probe array; and a detection device that is used for the method.

In order to solve the above-mentioned problems, the inventor of the present invention has found that, in manufacturing a substrate for immobilizing plural probes on an immobilization substrate, even in the case where the plural types of probes to be immobilized on a probe immobilization substrate to be obtained are the same as a whole, it is possible to realize encryption for types of probes spotted in respective spot addresses by changing spot positions where the respective probes are immobilized for each of probe immobilization substrates, for example, for each manufacture lot thereof, each manufactured substrate, each manufacturing day, each manufacturing month, each manufacturing apparatus, each manufacturing factory, each manufacturer, each using region, or each product revision, or an arbitrary point in time. In addition to such knowledge, the inventor of the present invention has verified that, when plural probes, which are capable of specifically binding to a target substance, are spotted on a substrate, it is possible to change a spotter, which is used in manufacturing a substrate for immobilizing plural probes on an immobilization substrate, to a spotter that makes it possible to change (the pattern of) positions to be spotted by the probes for the respective probe immobilization substrates according to predetermined information thereof. Eventually, the inventor of the present invention has completed the invention.

That is, according to the present invention, there is provided a spotter for spotting probes in spot portions that is used for manufacturing a probe immobilization substrate formed by immobilizing plural probes, which are capable of specifically binding to a target substance, in plural spot portions on a solid phase substrate, the spotter including: means for spotting the respective probes in accordance with a spot position pattern consisting of a group of spot addresses that assigns any one of the plural spot portions to each of the plural probes; and spot position pattern encrypting means for encrypting the spot position pattern according to predetermined information for each probe immobilization substrate to be manufactured.

At this time, the spot position pattern encrypting means may include a mechanism for storing plural spot position patterns applicable to the probe immobilization substrate and selecting one of the plural spot position patterns according to predetermined information for each probe immobilization substrate to be manufactured, and the spot position pattern encrypting means may have a function of changing the spot position pattern to be selected for each probe immobilization substrate to be manufactured. Alternatively, the spot position pattern encrypting means may include a mechanism for creating a new spot position pattern by applying encryption processing to a reference spot position pattern for each probe immobilization substrate to be manufactured with the predetermined information as a key, and the spot position pattern encrypting means may have a function of changing the spot position pattern to be created for each probe immobilization substrate to be manufactured.

Note that, in the spotter according to the present invention, the predetermined information may be individual information, which is set for each probe immobilization substrate to be manufactured, and may include at least a manufacturing lot number, a serial number, a manufacturing date and time, a manufacturing apparatus number, a manufacturer, a factory identification number, a manufacturing region number, a using region number, or a product revision number, which are used for identification of manufactured probe immobilization substrates, arbitrary information, or a combination of the pieces of information, or information that is unconditionally derived by analogy or calculation based on the pieces of information.

On the other hand, the spotter according to the present invention may further include, in correspondence to the spot position pattern encrypting means described above, means for marking a pattern number, which is affixed to the selected spot position pattern in advance, on the solid phase substrate or in a housing to be annexed to the solid phase substrate. Alternatively, the spotter may further include means for marking a key for canceling the encryption processing on the solid phase substrate or in a housing to be annexed to the solid phase substrate.

In addition, the means for spotting the respective probes may adopt a method of giving probes using an ink-jet technique.

The present invention also provides a probe immobilization substrate prepared by using the spotter according to the present invention. That is, according to the present invention, there is provided a probe immobilization substrate that is formed by immobilizing plural probes, which are capable of specifically binding to a target substance, in plural spot portions on a solid phase substrate, in which the spotting of the plural probes onto the solid phase substrate is performed using a spotter having any one of the above-mentioned constitutions. For example, the plural probes to be immobilized on the solid phase substrate may be DNA fragments, and the probe immobilization substrate may have a shape of a DNA micro array.

The present invention also relates to a detection device, which is provided with a function of decoding an encrypted spot pattern in the probe immobilization substrate according to the present invention and which makes it possible to perform detection of a target substance with plural probes on the probe immobilization substrate.

That is, according to the present invention, there is provided a detection device that detects in which one of plural spot portions each of plural probes in a probe immobilization substrate formed by immobilizing the plural probes, which are capable of specifically binding to a target substance, in the plural spot portions on a solid phase substrate, is spotted, the detection device including means for decoding a spot position pattern that is encrypted according to predetermined information for each probe immobilization substrate to be an object of detection. At this time; the spotting of the plural probes onto the solid phase substrate in the probe immobilization substrate is performed by the spotter according to the present invention including means for marking a pattern number, which is affixed to the selected spot position pattern in advance, on the solid phase substrate or in a housing to be annexed to the solid phase substrate. The detection device may include: means for reading the marked pattern number on the solid phase substrate or in a housing to be annexed to the solid phase substrate; and means for specifying a spot position pattern selected for the probe immobilization substrate based on the read pattern number and a group of pattern numbers that are affixed to the respective plural spot position patterns. Alternatively, the spotting of the plural probes onto the solid phase substrate in the probe immobilization substrate may be performed by a spotter including means for marking a key for canceling the encryption processing on the solid phase substrate or in a housing to be annexed to the solid phase substrate, and the detection device may include: means for reading the key for canceling the encryption; and means for specifying a spot position pattern created for the probe immobilization substrate by canceling the applied encryption in the course of creating the new spot position pattern based on the read key for canceling the encryption.

The present invention is also an invention of a dispensing device that is used in a process of dispensing plural probes to multi-well plates for a spotter in advance, for example, an invention of a dispensing device that is used in a process of dispensing plural probes to multi-well plates for a pin spot device in advance in an arrangement corresponding to a spot pattern when a pin spot method is applied to spotting of the respective probes. In other words, the present invention provides a dispensing device for dispensing plural probes that is provided with a mechanism that is capable of changing a position pattern for dispensing probes according to predetermined information in dispensing the probes.

That is, according to the present invention, there is provided a dispensing device for dispensing plural probes in a multi-well plate for a spotter, which is used for manufacturing a probe immobilization substrate formed by immobilizing the plural probes, which are capable of specifically binding to a target substance, in plural spot portions on a solid phase substrate, the dispensing device including: means for dispensing the respective probes in wells corresponding thereto on the multi-well plate in accordance with a spot position pattern consisting of a group of spot addresses that assigns any one of the plural spot portions to each of the plural probes; spot position pattern encrypting means for changing the spot position pattern according to predetermined information for each probe immobilization substrate to be manufactured; and means for allocating the wells on the multi-well plate in accordance with the spot position pattern that is changed for each probe immobilization substrate to be manufactured. Note that the dispensing device is used preferably when a pin spot device, which spots probes in spot portion according to a pin spot method, is used as a spotter. At this time, the spot position pattern encrypting means may include a mechanism for storing plural spot position patterns applicable to the probe immobilization substrate in advance and selecting one of the plural spot position patterns according to the predetermined information for each probe immobilization substrate to be manufactured, and the spot position pattern encrypting means may have a function of changing the spot position pattern to be selected for each probe immobilization substrate to be manufactured. Alternatively, the spot position pattern encrypting means may include a mechanism for creating a new spot position pattern by encrypting a reference spot position pattern for each probe immobilization substrate to be manufactured with predetermined information as a key, and the spot position pattern encrypting means may have a function of changing the spot position pattern to be created for each probe immobilization substrate to be manufactured.

Note that, the predetermined information may be individual information, which is set for each probe immobilization substrate to be manufactured, and includes at least a manufacturing lot number, a serial number, a manufacturing date and time, a manufacturing apparatus number, a manufacturer, a factory identification number, a manufacturing region number, a using region number, or a product revision number, which are used for identification of manufactured prove immobilization substrates, arbitrary information, or a combination of the pieces of information, or information that is unconditionally derived by analogy or calculation based on the pieces of information.

At the same time, the present invention also provides a program that is used in an operation for changing a position pattern for spotting or dispensing probes according to predetermined information in the spotter or the dispensing device according to the present invention.

That is, according to the present invention, there is provided a program executable by a computer by defining an operation for changing a spot position pattern, which is used for spotting plural probes, which are capable of specifically binding to a target substance, in plural spot portions on a solid phase substrate, in which information consisting of a group of spot addresses that assigns any one of the plural spot portions to each of the plural probes is defined as a spot position pattern, and in which the program includes: an operation for inputting predetermined information; an operation for specifying a corresponding spot position pattern according to the inputted predetermined information; and an operation for outputting the specified corresponding spot position pattern. At this time, the operation for specifying the corresponding spot position pattern according to the inputted predetermined information may include a procedure for specifying one spot position pattern, which is selected out of plural spot position patterns which are stored in advance and are applicable to a probe immobilization substrate to be manufactured, as the corresponding spot position pattern. Alternatively, the operation for specifying a corresponding spot position pattern according to the inputted predetermined information, which is defined by the program, may include a procedure for specifying a spot position pattern, which is created anew by applying encryption processing to a reference spot position pattern with the predetermined information as a key, as the corresponding spot position pattern.

Further, according to the present invention, there is provided a program executable by a computer for defining an operation for changing a spot position pattern, which is used for spotting plural probes, which are capable of specifically binding to a target substance, in plural spot portions on a solid phase substrate, in which information consisting of a group of spot addresses that assigns any one of the plural spot portions to each of the plural probes is defined as a spot position pattern, in which positional information of a group of wells, which associates the respective probes and the respective wells on the multi-well plate for a spotter in accordance with the spot position pattern, is defined as a dispense position pattern, and in which the program includes at least: an operation for inputting predetermined information; an operation for specifying a corresponding spot position pattern according to the inputted predetermined information; an operation for specifying a corresponding dispense position pattern by converting the specified corresponding spot position pattern to the dispense position pattern; and an operation for outputting the specified corresponding dispense position pattern. Note that the spotter may be a spot device according to a pin spot method. At this time, the operation for specifying a corresponding spot position pattern according to the inputted predetermined information may include a procedure for specifying one spot position pattern, which is selected out of plural spot position patterns which are stored in advance and are applicable to a probe immobilization substrate to be manufactured, as the corresponding spot position pattern. Alternatively, the operation for specifying a corresponding spot position pattern according to the inputted predetermined information may include a procedure for specifying a spot position pattern, which is created anew by encrypting a reference spot position pattern with the predetermined information as a key, as the corresponding spot position pattern.

Note that, in the program according to the present invention, the predetermined information may be individual information, which is set for each probe immobilization substrate to be manufactured, and includes at least a manufacturing lot number, a serial number, a manufacturing date and time, a manufacturing apparatus number, a manufacturer, a factory identification number, a manufacturing region number, a using region number, or a product revision number, which are used for identification of manufactured probe immobilization substrates, arbitrary information, or a combination of the pieces of information, or information that is unconditionally derived by analogy or calculation based on the pieces of information.

The present invention also provides a program for defining an operation for decoding an encrypted spot pattern for respective probes that are spotted on a probe immobilization substrate in the detection device according to the present invention. That is, according to the present invention, there is provided a program executable by a computer for defining an operation for decoding an encrypted spot pattern, which is used for a device for detecting in which one of plural spot portions each of plural probes in a probe immobilization substrate formed by immobilizing the plural probes, which are capable of specifically binding to a target substance, in the plural spot portions on a solid phase substrate, is spotted, in which information consisting of a group of spot addresses, which represents a spot portion in which each of the plural probes is spotted, is defined as a spot position pattern, and in which the program has a function of decoding a spot position pattern, to which encryption processing is applied according to predetermined information, for each probe immobilization substrate to be an object of detection, based on detection information obtained from the probe immobilization substrate, and the program includes: an operation for inputting the detection information obtained from the probe immobilization substrate; an operation for sampling partial information for decoding a spot position pattern in the probe immobilization substrate from the inputted detection information; an operation for decoding the spot position pattern in the probe immobilization substrate based on the sampled partial information; and an operation for outputting the decoded spot position pattern. In the program for decoding, the spotting of the plural probes onto the solid phase substrate in the probe immobilization substrate may be performed by the spotter according to the present invention which includes means for marking a pattern number, which is affixed to the selected spot position pattern in advance, on the solid phase substrate or in a housing to be annexed to the solid phase substrate, the partial information for decoding a spot position pattern in the probe immobilization substrate may be the marked pattern number, and the operation for decoding the spot position pattern in the probe immobilization substrate based on the sampled partial information may include a procedure for specifying the spot position pattern, to which the marked pattern number is affixed, as a decoded spot position pattern based on the marked pattern number and a pattern number affixed to each of the plural spot position patterns. In addition, in the program for decoding according to the present invention, the spotting in the probe immobilization substrate or onto the solid phase substrate of the plural probes is performed using the spotter according to the present invention that includes means for marking a key for canceling encryption of the encryption processing on the solid phase substrate or in a housing to be annexed to the solid phase substrate. The partial information for decoding a spot position pattern in the probe immobilization substrate is a key for canceling the encryption, which is marked on the solid phase substrate of the probe immobilization substrate or in the housing to be annexed to the solid phase substrate. The operation for decoding a spot position pattern in the probe immobilization substrate based on the sampled partial information can include a procedure for specifying a spot position pattern created for the probe immobilization substrate as a decoded spot position pattern by canceling the applied encryption based on the key for canceling the encryption.

Further, the present invention provides the program according to the present invention in a form of a computer readable recording medium in which the program is represented in a computer executable representation form. That is according to the present invention, there is provided a computer readable recording medium having stored thereon at least one program that is represented in a computer executable representation form, in which at least one or more of the programs is a program according to the present invention having any one of the structures described above.

Finally, the present invention provides a gene diagnosis system constituted by combining the probe immobilization substrate and the detection device according to the present invention. In other words, the gene diagnosis system according to the present invention is a gene diagnosis system for using a probe immobilization substrate, which is formed by immobilizing plural probes capable of specifically binding to a target substance in plural spot portions on a solid phase substrate, to allow a target substance in a specimen to bind to probes, which are capable of specifically binding to the target substance on the probe immobilization substrate, and then detecting the bound target substance. The probe immobilization substrate to be used is the probe immobilization substrate according to the present invention having any one of the above-mentioned constitutions, and the detection device according to the present invention having any one of the above-mentioned constitutions is used for detection of the bound target substrate.

In addition, for the purpose of use in the present invention, the present invention provides a recording substrate having recorded thereon plural kinds of spot position patterns prepared in advance that are recorded. In other words, one of the recording media according to the present invention is a recording medium having recorded thereon plural kinds of spot position patterns for the spotter according to the present invention. A spot position pattern encrypting means in the spotter is provided with a mechanism for storing plural spot position patterns, which can be applied to the probe immobilization substrate; in advance and selecting one of the plural kinds of spot position patterns according to predetermined information for each probe immobilization substrate to be manufactured, and has a function of changing the spot position pattern to be selected for each probe immobilization substrate to be manufactured.

In addition, one of the recording media according to the present invention is a recording medium having recorded thereon plural kinds of spot position patterns for the dispensing device according to the present invention. A spot position pattern encrypting means in the dispensing device is provided with a mechanism for storing plural spot position patterns, which can be applied to the probe immobilization substrate, in advance and selecting one of the plural kinds of spot position patterns according to predetermined information for each probe immobilization substrate to be manufactured and has a function of changing the spot position pattern to be selected for each probe immobilization substrate to be manufactured.

Further, one of the recording media according to the present invention is a recording medium having recorded thereon plural spot position patterns for the detection device according to the present invention. In the detection device, the spotting in the probe immobilization substrate to be a target or onto the solid phase substrates of the plural probes is performed using the spotter of the present invention. The detection device includes: means for reading the pattern number that is marked on the solid phase substrate of the probe immobilization substrate or in a housing to be annexed to the solid phase substrate; and means for storing pattern numbers affixed to the respective plural spot position patterns in advance and a group of spot addresses corresponding to the pattern numbers and specifying a spot position pattern that is selected for the probe immobilization substrate based on the pattern number to be read.

According to the present invention, encryption of a spot pattern for changing spot addresses of plural probes immobilized on a probe immobilization substrate can be performed easily. Thus, for example, even if a combination result itself of a target substance remaining on a DNA chip after use such as a DNA chip for gene diagnosis is equivalent to individual information on each patient, and a third party observes such DNA chip after use, it becomes less likely that the diagnosis result is easily decoded by the third party from the used DNA chip since a probe immobilization order thereof is encrypted.

Moreover, concerning plural probes themselves that are used for preparation of a probe immobilization substrate used in the medical field, for example, respective DNA probes on a DNA chip, information concerning a target substance to be an object of detection is disclosed. However, when a social position of a source of provision of base sequences of the DNA probes is taken into consideration, the base sequences themselves of the respective DNA probes may be excluded from the information to be disclosed. In addition, when base sequences of DNA probes used in diagnosis are decoded, a problem of maintenance of confidential information also occurs. For example, the base sequences are copied by a third party that is not permitted to use the base sequences. From those viewpoints, the use of the present invention prevents a third party from easily decoding base sequences of DNA probes constituting a DNA chip. This contributes significantly in preventing decoding for the purpose of copying.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 is a diagram schematically showing an example of a method of selecting a spot position pattern in an operation for changing the spot position pattern in assigning spot addresses for respective probes on a probe immobilization substrate in a spotter according to the present invention, and a data flow corresponding to the selection operation;

FIG. 2 is an explanatory diagram showing examples of a spot pattern at the time when sixteen types of probes are spotted in a micro array shape;

DESCRIPTION OF THE PREFERRED EMBODIMENTS

Figure 3:
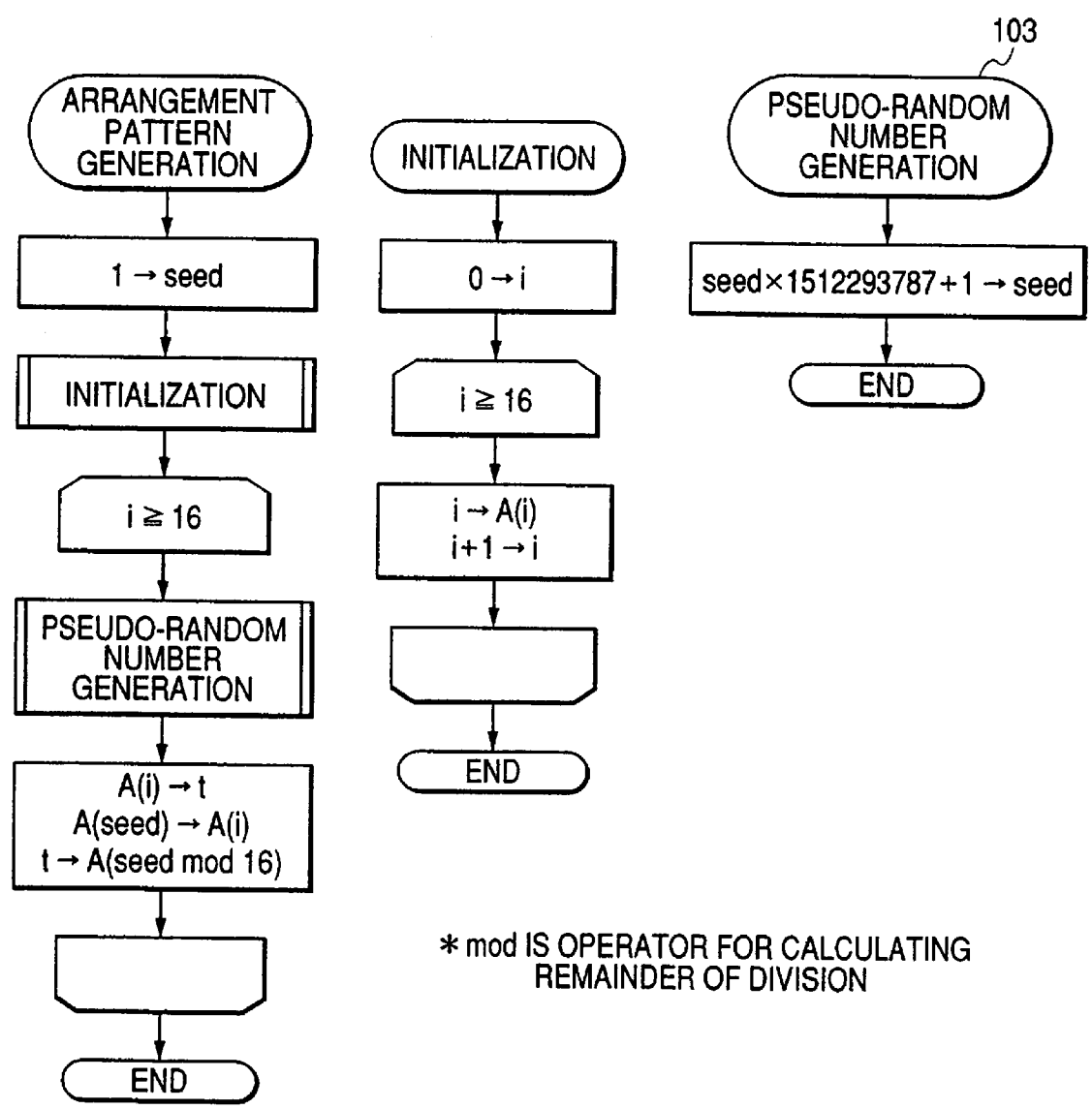
FIG. 3 is a diagram showing an example of an algorithm for creating a spot pattern at the time when sixteen types of probes are spotted in a micro array shape using an algorithm for pseudo-random number generation.

Preferred embodiments of the present invention will now be described in detail in accordance with the accompanying drawings.

In manufacturing a substrate for immobilizing plural probes on an immobilization substrate, even in the case where plural types of probes to be immobilized on a probe immobilization substrate to be obtained are identical to each other, a spotter according to the present invention makes it possible to realize encryption for types of probes spotted in respective spot addresses by changing, in each of probe immobilization substrates, spot positions where the respective probes are immobilized, for each manufacture lot thereof, each manufacturing substrate, each manufacturing day, each manufacturing month, each manufacturing apparatus, each manufacturing factory, each manufacturer, each region to be used, or each product revision, or at an arbitrary point in time.

In the probe immobilization substrate that is an object of the present invention, a solid phase substrate on which plural probes are spotted and immobilized is selected appropriately according to an application of a probe immobilization substrate to be prepared. The solid phase substrate itself is not specifically limited. For example, in the case where the probe immobilization substrate is a micro array type on which plural probes are spotted in array and immobilized, when convenience of use in target substance detection using such a probe of a micro array type and high versatility are taken into account, glass substrates and plastic substrates, which are solid phase substrates showing a plane surface, can be used preferably. Among the glass substrates, a no-alkali glass substrate and a quartz substrate, which do not include an alkali component in a substrate material itself, are examples of more preferable substrates. In addition, concerning these solid phase substrates, various immobilization methods, which are usable in a process of spotting various probes on a surface thereof and immobilizing the probes, have already been reported.

As a method of immobilizing probes on a substrate, various methods have already been proposed for each type of the probes and used according to a purpose thereof. For example, there are known a method of preparing DNA probes immobilized on a substrate by applying a solid phase synthesis method to DNA probes and performing synthesis of DNA molecules having a target base sequence on the substrate and a method of giving DNAs, which are prepared separately, onto a substrate and then binding the DNAs on the substrate and immobilizing the DNAs. Note that, in a spot operation for giving the separately prepared DNAs onto the substrate, a method such as a pin method, a stamp method, or an ink-jet method is used.

As a method of synthesizing DNA probes that are arranged in array on a substrate, for example, as disclosed in U.S. Pat. No. 5,143,854, there is known a method of synthesizing polymers (DNA molecules) having a target base sequence on a substrate by repeating an operation of removing a protecting group at an end of 5' from a selected region on a solid phase synthesized substrate with an activator and causing a monomer having a removable protecting group to act on the selected region to combine the selected region with the end of 5'.

Usually, the spotter according to the present invention adopts a method of spotting probes, which are separately prepared, on a surface of a substrate and immobilizing the probes. However, the spotter also includes an apparatus that adopts a method of applying the above-mentioned solid phase synthesizing method to synthesize target probes on a substrate to immobilize the probes in spot addresses (portions) to thereby attain an equivalent spot state.

In addition, as a method of spotting probes, which are prepared in advance, on a substrate and then immobilizing the probes on a surface of the substrate, for example, as disclosed in JP 8-23975 A, there is known a method of preparing a substrate itself with a high-molecular compound having a carbodiimide group, or carrying a material layer for immobilization, which is composed of a high-molecular compound having a carbodiimide group, on a substrate and then bringing a biologically active substance, which has reactivity with respect to the carbodiimide group, into contact with the high-molecular compound having the carbodiimide group present on the surface of the substrate to thereby perform covalent immobilization of probes with a reaction to the carbodiimide group. Further, as disclosed in JP 8-334509 A, in detection of a biologically active substance, there is known a detection method of forming covalent bonding via a carbodiimide group on a compound containing the carbodiimide group to thereby immobilize probes.

Moreover, JP 2001-178442 A discloses a method of bringing a DNA fragment having a thiol group (—SH) at an end thereof, which can be introduced using a thiol modifier, and a solid phase carrier, in which chain molecules having a reactive substituent that can react with the thiol group (—SH) to form covalent bonding are immobilized on a surface at another end different from a chain end where the reactive substituent is located, into contact with each other in a liquid phase to thereby form covalent bonding between the DNA fragment and the chain molecules with a reaction of the thiol group (—SH) and the reactive substituent and immobilize the DNA fragment to a surface of the solid phase carrier. In addition, JP 2001-178442 A also mentions that, as an example of the reactive substituent that can react with the thiol group (—SH) to form covalent bonding, a substituent containing a reactive functional group, which is selected out of a group consisting of a maleimidyl group, an α, β-unsaturated carbonyl group ($>C=C=O$), an α-halocarbonyl group (—COX), an alkyl halide group (—($C_nH_{2n}$)—X), an aziridine-2-yl group, and a disulfide group (—S—S—) is usable.

Concerning a method of immobilizing various probes spotted on a substrate, as described above, many methods are know only as an immobilization method for a DNA fragment.

Note that, in the present invention, types of probes to be spotted and methods and mechanisms of immobilization for the same are not specifically limited.

In addition, as a method of spotting probes on a substrate, there is a method of giving an aqueous solution, in which probes are dissolved or scattered in an aqueous medium, to a surface of the substrate, for example, a method of spotting probes on a surface of a substrate having a basic group with an ink-jet method disclosed in JP 11-187900 A, or a pin method or a pin & ring method.

Concerning a spotting method using an aqueous solution of probes, among the above-mentioned various spotting methods, in particular, the ink-jet method is a spotting method that is used preferably for the present invention because the ink-jet method is capable of spotting probes in highly dense and accurate positions. Moreover, in the case where a surface of a substrate on which probes are spotted is an electrode or the like, if the ink-jet method for spotting probes in a non-contact manner is used, there is also an advantage that a surface of the electrode or the like is not damaged due to mechanical contact compared with the pin method that involves contact by a pin. In the spotting according to the ink-jet method, there is used a procedure of pouring liquid containing probes into a very fine nozzle, and instantly pressurizing or heating a part near this nozzle to cause a droplet containing a very small amount of probes to spew from a tip of the nozzle, fly in the space, and adhere to a surface of a substrate. In that case, there is an advantage that, although an amount of droplet to be discharged from the nozzle is very small, the amount shows high reproducibility. In the spotting method according to the ink-jet method for controlling an amount of droplet to be discharged to a very small amount accurately, a medium component constituting the liquid containing probes is not specifically limited as long as the medium component does not substantially affects the probes of the medium and satisfies a medium composition, which can be normally discharged using the ink-jet head, when the droplet is discharged from an ink-jet head. For example, in the case where the ink-jet head to be used is a bubble jet head provided with a mechanism for giving thermal energy to a medium to discharge the medium, an aqueous medium containing glycerol, thiodiglycol, isopropyl alcohol, or acetylene alcohol is preferable as a medium component contained in a liquid containing probes. For example, when the probes are DNA fragments, an aqueous medium containing glycerol of 5 to 10 wt %, thiodiglycol of 5 to 10 wt %, or acetylene alcohol of 0.5 to 1 wt % is preferably used. In addition, in the case where an ink-jet head to be used is a piezo jet head that discharges liquid using a piezoelectric element, an aqueous medium containing ethylene glycol or isopropyl alcohol is preferable as a medium component contained in a liquid containing probes. For example, when the probes are DNA fragments, an aqueous medium containing ethylene glycol of 5 to 10 wt % or isopropyl alcohol of 0.5 to 2 wt % is used preferably.

When the liquid containing probes, which is prepared using the aqueous medium having the medium component, is discharged from the ink-jet head and adhered on a substrate, a shape of a droplet spot is circular, and a spot range of the adhered droplets does not expand following running of the aqueous medium. In the case where droplets containing probes are spotted densely, a phenomenon where the aqueous medium oozes out between spots adjacent to each other and the spots are joined can be controlled. Moreover, when the ink-jet method is used, spot address control such as deciding which probes are spotted in which positions can be easily changed by a program. Thus, the ink-jet method is a preferable spot method in the present invention in which spot addresses of respective probes are required to be changed. Note that, in the present invention, a composition of an aqueous medium, which is used for preparation of liquid containing probes to be spotted, is not limited to the compositions described above as examples.

The probe immobilization substrate can carry out detection or quantitative determination for plural target substances contained in a sample simultaneously using plural probes immobilized on the substrate. Because of this advantage, for example, a DNA chip is suitable for analysis of expression of plural types of genes or monobasic polymorphic analysis and has at least two large application fields, that is, an application in a research field in which these gene analyses are used and an application in a medical field in which gene diagnosis is performed. In the case where a DNA chip is used for the application of gene diagnosis, a DNA chip used for diagnosis of each patient indicates a result of the gene diagnosis. If a portion where probes immobilized on the DNA chip is present and a name of a patient for whom this DNA chip was used are found, even a third party can interpret the diagnosis result that is personal information of the patient. In that case, when immobilized plural types of probes are the same DNA chips, by changing spot positions (patterns) of the respective probes and performing treatment for preventing a third party from easily specifying a portion where the proves immobilized on the DNA chip are present, even if the third party obtains a used DNA chip, it becomes far less likely that the diagnosis result of each patient is analyzed without permission.

As an example of a method of changing a spot position (pattern) of each probe, which is used in the spotter according to the present invention, there is a method of, for each probe immobilization substrate, for example, in accordance with the process shown in FIG. 1, preparing plural types of spot patterns 203, which are created in advance, according to product information (probe information) 201 of the spotter and carrying out selection 204 of one type of spot pattern from plural types of spot patterns (a collection of spot patterns) 203, which are created in advance, on the basis of a manufacturing number (serial number) 202. Each probe immobilization substrate creates a spotter control command 205, which controls arrangement of probes to be spotted on respective spot addresses by the spotter in accordance with the selected one type of spot pattern 204 as needed, and changes an operation 206 of the spotter. For example, in the case where sixteen types of probes are spotted in sixteen spot addresses arranged in matrix, as shown in FIG. 2, the probe immobilization substrate selects, for example, a set of ten types of spot patterns as a collection of spot patterns 203 among a large number of spot patterns created in advance. Note that reference numeral 101 denotes the spotted respective probes. After changing the manufacturing number (serial number) 202 to a natural number for each probe immobilization substrate, if a numeral of a last one digit is 1, a pattern of a pattern number 1 is changed, and if a numeral of a last one digit is 2, a patter of a pattern number 2 is changed. In this way, spot patterns are changed in accordance with manufacturing numbers (serial numbers).

Note that in the respective spot patterns shown in FIG. 2, numerals shown in respective spot addresses are numbers indicating sixteen types of probes (hereinafter referred to as probe numbers). In any spot pattern, the probes indicated by the respective probe numbers represent the same probe types. In that case, information on what kinds of probe types the respective probe numbers are, which are common to a group of these probe immobilization substrate, is equivalent to product information (probe information). In addition, there are 16! ways in total as methods of arranging sixteen types of probes in sixteen spot addresses (spot patterns). A total number of methods of selecting ten spot patterns with pattern numbers 1 to 10 out of the patterns amounts to an enormous number of (16!)·(16!−1)...(16!−9)·(16!−10). In other words, the selection itself of the collection of spot patterns of the pattern numbers 1 to 10 shown in FIG. 2 is already in an encrypted state in which probability of performing the same selection is extremely low. Therefore, concerning each probe immobilization substrate, even if a simple selection criterion for selecting a pattern number which is the same as a last one digit of the manufacturing number (serial number) 202 thereof, the selection is in a highly encrypted state.

In addition, in an operation for selecting one pattern number out of a collection of spot patterns on the basis of the manufacturing number (serial number), if the selecting operation is made more complicated, a more highly encrypted state is achieved. For example, by adopting a selection criterion in which the number of types of patterns constituting the collection of spot patterns is changed to n and the manufacturing number (serial number) represented in a natural number in the decimal system is converted into representation in the n-ary, and then a pattern number that is the same as a numeral of the last one digit of the manufacturing number (serial number) is selected, since a third party cannot estimate that the conversion operation from the decimal system to the n-ary is included, the selection is in a more highly encrypted state. Alternatively, if a selection criterion is adopted in which some arithmetic processing is applied to a numerical value of the manufacturing number (serial number) represented in a natural number in the decimal system, for example, a value, which is obtained by adding up numerals of respective digits, is represented in the n-ary, and a pattern number that is the same as a numeral of the last one digit of the manufacturing number (serial number) is selected, since a third party cannot estimate that a numerical value processing operation of plural stages is included, the selection is in a still more highly encrypted state.

In the above explanation, for the purpose of simplifying the explanation, the example is used in which the number of types of probes and the number of spots (the number of spot addresses) are equal to each other. However, actually, the number of types of probes of spot patterns prepared for encryption and the number of probes necessary for an actual product are not required to be the same. In addition, it takes time to prepare spot patterns corresponding to the number of probes necessary for an actual product, and management for the spot patterns may be complicated. For example, in the case where the number of types of probes is smaller than the number of spots (the number of spot addresses), types of probes to be actually spotted may be spotted to spot addresses to which probe numbers thereof are assigned in each spot pattern to bring excess spot addresses into an idle state. For example, the example shown in FIG. 2 shows a spot pattern for probes of sixteen types. If the number of types of probes to be actually used is ten, there is a method of spotting the probes to spot addresses for probe numbers 1 to 10 and no probe is spotted to spot addresses for probe numbers 11 to 16. In that case, concerning assignment of probe numbers to types of probes to be actually used, it is also possible to further encrypt the assignment or select probe numbers from other patterns.

Instead of providing addresses in an idle state to which no probe is spotted it is also possible that plural dummy probes or same probes are spotted. To explain specifically using the example described above, for example, there is a method of redundantly spotting probes, which do no directly relate to a detection object of a product, or probes, which have already been spotted to other positions (addresses) such as the probe numbers 1 and 2, as dummy probes in the spot addresses for the probe numbers 11 to 16. In this case, it becomes more difficult for a third party to interpret a diagnosis result than in the case where the selection of probes is simply encrypted.

In addition, in the example of FIG. 2, the spot addresses to which the respective probes are spotted have a matrix shape arranged on a square. However, a shape of the spot addresses is not limited to this matrix shape, and spots may be arranged in a rectangular shape in which the vertical number of spots and the horizontal number of spots are different, or a polygonal shape, or may be arranged in a honeycomb shape for the purpose of increasing density of the spots. The matrix shape is not specifically limited.

In addition, in the case where the number of types of probes n is larger than the number of spot addresses m, two types of probes may be mixed and spotted for one spot address.

On the other hand, when spot patterns are selected on the basis of predetermined information characteristic to respective probe immobilization substrates as described above, a method may be adopted in which predetermined information to be used is used as predetermined information to be changed among the respective probe immobilization substrates by converting, other than manufacturing numbers (serial numbers), for example, manufacturing dates and times into serial numerical values. It is needless to mention that the information may be a random value that is given for each probe immobilization substrate or may be numerical values including a manufacturing lot number, a manufacturing apparatus number, a manufacturing region number, a using region number, a product revision number, or the like. Note that, in the present invention, an operation for selecting spot patterns on the basis of the predetermined information characteristic to the respective probe immobilization substrates is not limited to the example described above.

In addition, a collection of spot patterns does not always have to be incorporated in a spotter. For example, it is also possible that the spotter is provided with a device with which the collection of spot patterns can be inputted, and the collection of spot patterns is inputted at appropriate time. More specifically, it is also possible that the spotter is provided with a floppy disk reading device, and the collection of spot patterns recorded in the floppy disk in advance is read to be inputted to the spotter from the reading device.

On the other hand, when judging the presence or absence of a target substance specifically binding to respective probes using the respective probe immobilization substrates on which spots are formed using the spotter according to the present invention, it is desirable that a person using the probe immobilization substrates is capable of simply recognizing when the person detects probes of which probe numbers are arranged on respective spot addresses in a probe immobilization substrate that the person is using. Taking this point into account, it is desirable to, in each prove immobilization substrate, write information on which spot pattern is used in a region other than a probe immobilization portion in a micro array thereof, a housing for the probe immobilization substrate, or the like. As a method of writing information on a used spot pattern and the like, a two-dimensional code, a bar code, a calra code, and the like are conceivable. However, the method is not limited to these code representation methods. For example, in the case where means for observing respective probe immobilization substrates with a fluorescent scanner is used in detecting results in the probe immobilization substrates, if a method is adopted in which a two-dimensional code is drawn using a fluorescent substance in a region where probes are not immobilized in a micro array, and fluorescence by this two-dimensional code is detected by the fluorescent scanner, a new diction device is not required. Thus, this method is desirable.

Note that the housing in this context includes not only housings in a narrow sense, for example, a protective material and a structural support for protecting a probe immobilization substrate from a contaminant, a physical impact, and the like but also housings in a wide sense, which mean accessories that can be provided integrally with the probe immobilization substrate, such as a package and a packing material as products, documents like a user instruction, and other information recording media.

Figure 4:
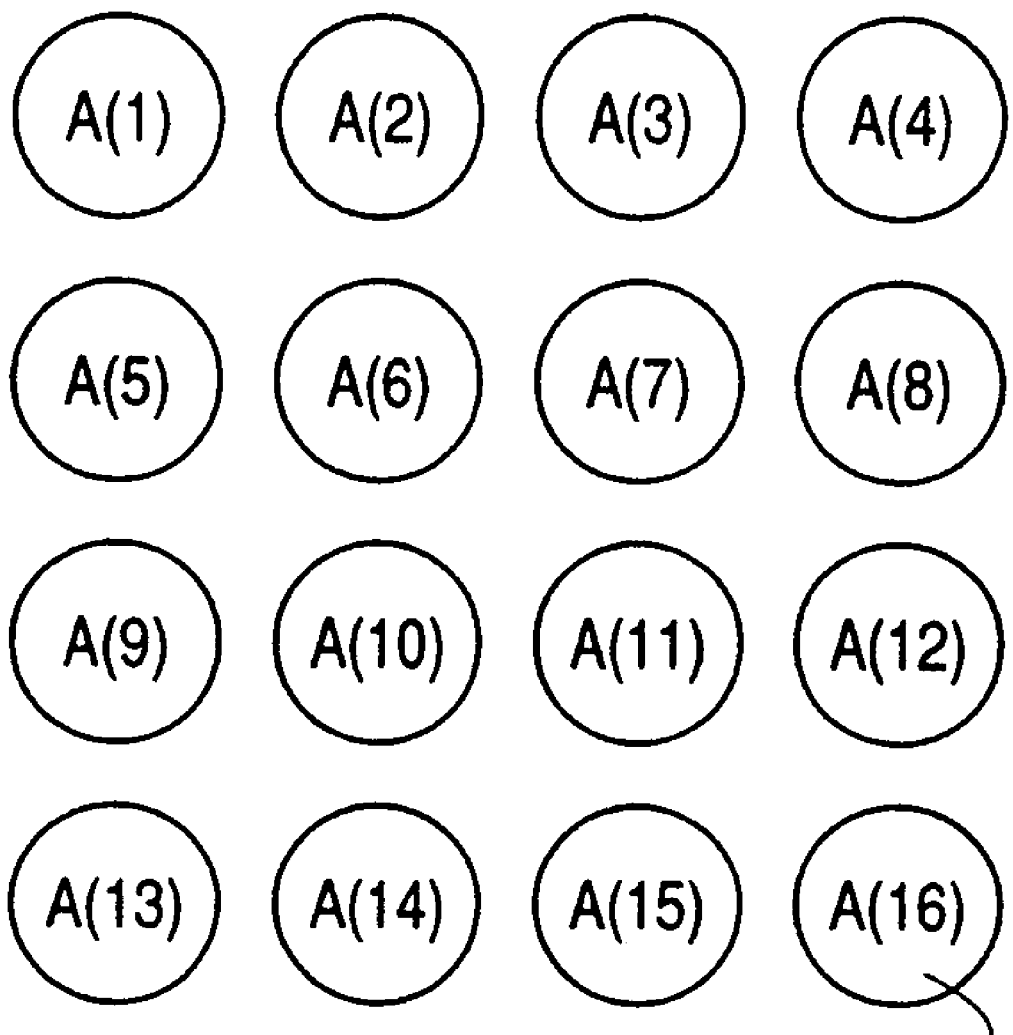
FIG. 4 is an arrangement diagram showing probe types (probe numbers), which are assigned to respective spot addresses of a micro array shape, in a spot pattern to be created.

In addition, in selecting spot patterns on the basis of predetermined information characteristic to the respective probe immobilization substrate, instead of the method of selecting spot patterns from the collection of spot patterns composed of spot patterns determined in advance, a method of creating spot patterns on the basis of predetermined information as needed may be adopted. For example, in the case where sixteen types of probes are spotted to sixteen spot addresses, it is also possible to create a random number sequence, in which probe numbers are rearranged, A(1), A(2), ... A(16) on the basis of predetermined information, for example, manufacturing numbers (serial numbers) in accordance with an algorithm for arrangement pattern generation shown in FIG. 3, and apply the probe numbers to a matrix arrangement of the sixteen spot addresses in accordance with this random number sequence, thereby creating one spot pattern as shown in FIG. 4. Reference numeral 102 in FIG. 4 denotes an encrypted probe number on a spot. In other words, in the algorithm shown in FIG. 3, in a step of generating a pseudo-random number sequence, a value of a seed, which is unconditionally selected, is adopted on the basis of predetermined information such as a manufacturing number (serial number) to generate a series of pseudo-random number sequence. If, for example, a value, which is the same as a numeral of a last one digit of a manufacturing number (serial number) represented in a natural number in the decimal system, is selected as a value of a seed, which is unconditionally selected on the basis of predetermined information such as a manufacturing number (serial number) for each probe immobilization substrate, ten types of spot patterns different from each other are generated.

In the present invention, the random number sequence means a sequence in which an arrangement of the sequence $x_1, x_2, x_3, \ldots$ is irregular in appearance, possibility of an arbitrary $x_k$ being smaller than C depends only on C and does not depend on $x_{k-1}$. In particular, a sequence in which the sequence $x_1, x_2, x_3, \ldots$ consist of natural numbers are usually used in the present invention.

Random numbers include a random number with uniform distribution, in which natural numerical values in a certain range appear with an equal probability, such as a so-called pip of a dice, and a random number with various probability distributions, in which numbers appear with unequal probability, such as a chi-square distribution, a gamma distribution, a triangle distribution, a normal distribution, a power distribution, a logistic distribution, and a Poisson distribution. In the present invention, a type of a random number to be used is not limited. However, usually, it is preferable to use a random number with uniform distribution.

When a random number sequence is used in a computer or the like, in general, a pseudo-random number, which is generated on the basis of a predetermined algorithm, is used. In addition, as an algorithm for generation of a pseudo-random number with uniform distribution that is usable in a computer or the like, there are known plural methods such as the linear congruential method (103), the Knuth random number generation method, the M-sequence random number, and the Wichmann-Hill random number generation method. Note that, in the present invention, when the pseudo-random number with uniform distribution is used, the algorithm to be applied for generation of the pseudo-random number with uniform distribution is not specifically limited.

In many of pseudo-random number generation algorithms, which are known conventionally, when a numeral to be a basis for generating a pseudo-random number sequence, which is called a seed, is given, different pseudo-random number sequence are generated according to the seed. Note that, in this algorithm, since one pseudo-random number sequence is generated for each value of the seed, if a value of each used seed is known, it is possible to generate the same pseudo-random number sequence again. If this characteristic is used to make an arrangement such that a type of a pseudo-random number generation algorithm, which is used at the time of spot pattern generation in an initial spot process, and a value of a seed therefor can be specified at the time of detection, a selected spot pattern can be generated again in a probe immobilization substrate for probes for the detection. In other words, at the time of detection, it is possible to judge in what kind of spot pattern each probe in the probe immobilization substrate is spotted.

The type of the pseudo-random number generation algorithm, which is used at the time of generation of spot patterns in the initial spot process, may be selected in advance. On the other hand, for example, it is possible that a manufacturing number or a manufacturing date and time of the probe immobilization substrate is converted into a value of serial natural numbers, and this value is used as the value of the seed. Alternatively, instead of the manufacturing number or the manufacturing date and time, a manufacturing lot number, a manufacturing apparatus number, or the like may be used. Moreover, a value to be set at random may be used as long as the value is a value unique to the probe immobilization substrate. Note that, at the time of detection, when it is taken into account that the spot patterns are distinguished using the value of the seed used by the probe immobilization substrate, for example, in the case where the probe immobilization substrate is a micro array, it is desirable to write the value of the used seed as a decryption key in a region other than a probe immobilization position in the micro array, a housing to be provided with the probe immobilization substrate, or the like. For example, in the case where a detection method for using a fluorescent scanner to observe a probe result obtained by using the probe immobilization substrate is adopted, for example, information including the value of the seed is converted into a two-dimensional code and drawn using a fluorescent substance in a position where the probes in the micro array are not immobilized to detect this fluorescence with the fluorescent scanner. Consequently, in addition to the probe result, information of the two-dimensional code can also be read. This form of writing the information, which includes the value of the seed, using the fluorescent substance is one of preferable methods because a new detection device is not required.

The algorithm for generating spot patterns and the algorithm for pseudo-random number generation, which are used in the spotter according to the present invention, are not limited to the ones described above as examples. In addition, as a method of marking a decryption key, the two-dimensional code, the bar code, the calra code, and the like are described above as examples. However, the method of marking a decryption key is not limited to these methods.

Moreover, the function for changing spot patterns does not have to be incorporated in a manufacturing apparatus for a substrate having plural probes. For example, a method of generating several spot patterns on a computer in advance, converting the spot patterns into operation description data of the manufacturing apparatus, and replacing the data at a certain point in time to substantially change the spot patterns is also possible.

As described above; in the spotter according to the present invention, when positions where probes are spotted on a probe immobilization substrate are changed, it is preferable to adopt the ink-jet method having an advantage that the positions can be changed easily. In addition, in the case where the pin method is adopted for spotting, in general, liquid containing respective probes is dispensed to a well plate, and the liquid dispensed to respective wells is sampled at points of respective pins to be spotted in corresponding positions. Compared with the ink-jet method, in the case of this pin method, positions where probes can be spotted and an order of spotting the probes are limited by an arrangement of pins to be used. Thus, a method may be adopted in which, when probes are dispensed to the well plate, types of the probes to be dispensed to the respective wells, that is, dispensing patterns are changed to change types of probes to be spotted to the respective spot addresses, whereby the spot patterns are changed substantially.

In addition, the use of the well plate is not limited to the pin method. In the ink-jet method, for example, it is possible that a procedure is adopted in which, when a medium containing plural types of probes is injected, into an ink-jet head, which is capable of spotting plural media containing probes simultaneously, the medium containing these probes is dispensed to a well plate in advance and is supplied to the ink-jet head from the well plate. In that case, there is also a method in which a device and a program for driving the ink-jet head are fixed, and when the probes are dispensed to the well plate, the dispensing patterns are changed to change the spot patterns.

A detection result for a target substance in a probe immobilization substrate, which is prepared by using the above-described spotter according to the present invention, can be detected using the applied label for example, in a DNA chip, after hybridization reaction with a labeled target substance. In that case, a detection unit to be used is different depending upon how the target substance is labeled. For example, in the case where the label is a fluorescent label using a fluorescent substance such as rhodamine, the detection unit is a fluorescent scanner, a fluorescent microscope, or the like that is capable of observing the fluorescent label. Note that a method of labeling a target substance and a detection method corresponding thereto are not limited to the fluorescent label described as an example.

On the other hand, in the detection, spot addresses where specific binding of probes to some target substance is attained are found. However, if types of the probes arranged in the spot addresses cannot be recognized, interpretation of a detection result cannot be performed to find between which probe and the target substance a binding reaction has occurred. Therefore, it is necessary to, simultaneously with the detection, specify types of probes arranged in the respective spot addresses, that is, spot patterns to interpret which probe has reacted with the target substance.

For example, in the case where information such as spot pattern numbers, a seed of a pseudo-random number used for generation of spot patterns, and a decryption key is marked on a probe immobilization substrate, it is possible to simultaneously detect these pieces of information to decode spot patterns corresponding to the information. On the other hand, in the case where information such as a spot pattern number and a decryption key is marked in a housing to be annexed to the probe immobilization substrate, a package, which houses the probe immobilization substrate, included in the concept of the housing in this context, or the like rather than the probe immobilization substrate, and the information cannot be detected simultaneously, it is necessary to read the information separately and input the information to a decoding device.

As a method of inputting the information such as a spot pattern number and a decryption key separately, a method of using input by a keyboard attached to a decoding device and a method of separately providing code reader for a bar code, a two-dimensional code, calra code to read and input a code are possible. However, the method of inputting the information is not limited to these methods. Note that it is possible to carry out decode processing independently after a detection operation is finished. Therefore, the decoding device may be provided separately from a detection device or may be incorporated in the device.

In the case where the information such as a spot pattern number, a seed of a pseudo-random number, and a decryption key, is marked on a probe immobilization substrate, and the information is read using the same detection unit simultaneously with detection of a target substance bound to probes, a mechanism for reading and decoding the information is incorporated in the detection device, whereby decoding can be performed simultaneously with a detection operation.

In the case where a fluorescent substance is used for labeling for a target substance to detect fluorescence, if the above-mentioned information such as a spot pattern number, a seed of a pseudorandom number, and a decryption key is marked using the fluorescent substance in a region where probes are not immobilized, a new detection device is not required. Thus, this method is preferable.

Figure 5:
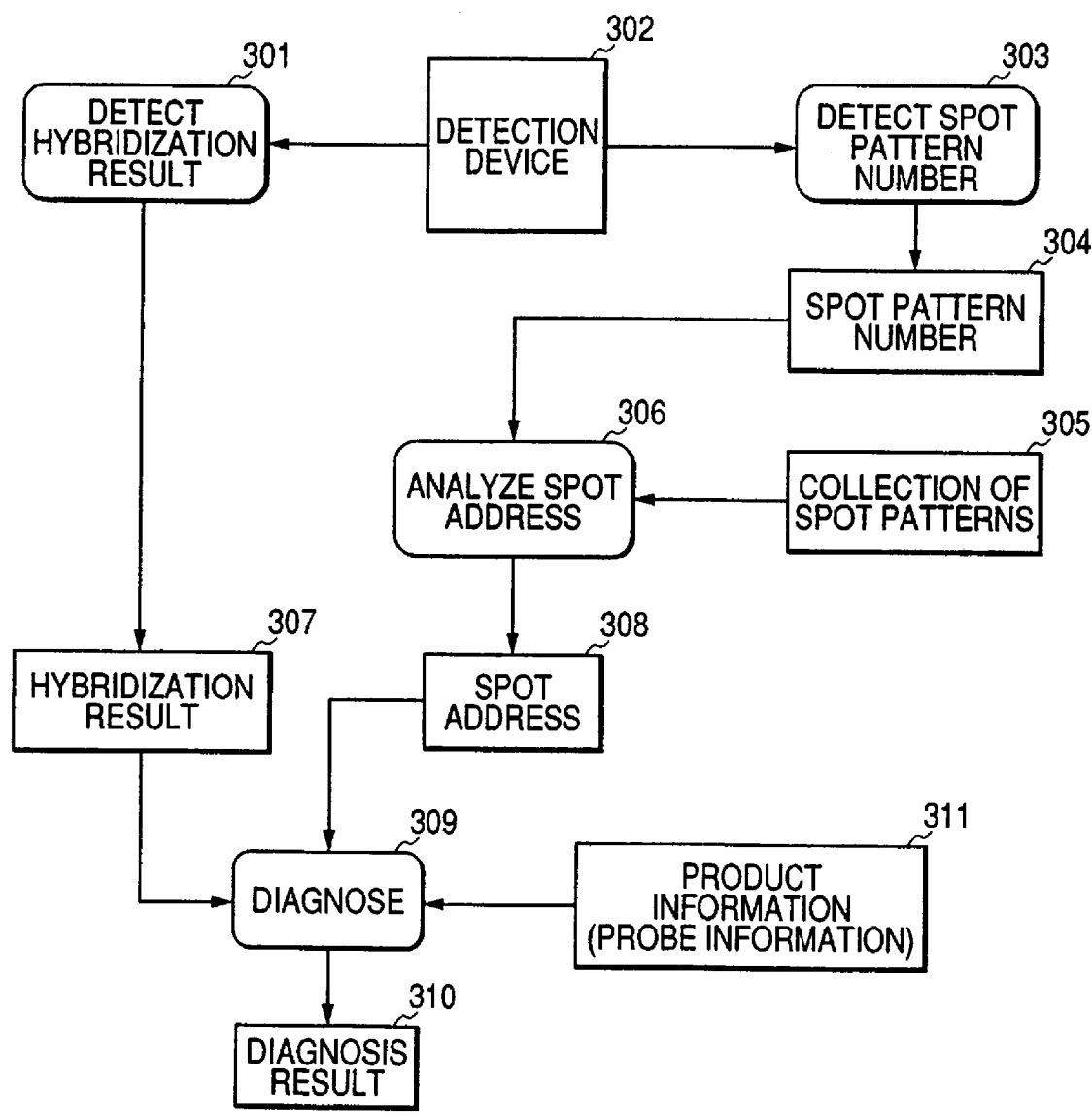
FIG. 5 is a diagram schematically showing an example of judgment of spot addresses of respective probes on a probe immobilization substrate and an association operation for detection results for the respective probes based upon a detection result for the probe immobilization substrate in a detection device according to the present invention and information on spot pattern numbers, and a data flow corresponding to the operation.

As an example of a device configuration in the detection device according to the present invention, an example of a device configuration that is applicable to a probe immobilization substrate, in which a fluorescent substance is used for labeling for a target substance, and information on a spot pattern number is also written to the probe immobilization substrate using the fluorescent substance, can be shown in FIG. 5. When the probe immobilization substrate takes a form of a DNA chip, after applying the hybridization reaction to a sample, the fluorescent substance is affixed to the target substance as a label in advance, and presence or absence of a target substance, which has formed a specific hybrid with probes as a result of the hybridization reaction, and an amount of the target substance are observed by a detection device 302 for fluorescent observation. Simultaneously with a detection operation 301 for a result of the hybridization, a portion where the spot pattern number is marked with the fluorescent substance on the probe immobilization substrate is also observed by the detection device 302. As a result, in the detection operation 301 for a result of the hybridization, a spot address where presence of the fluorescent label is observed, or a result of measurement of an amount thereof is obtained as a hybridization result 307 once. By the observation of the portion where the spot pattern number is marked with the fluorescent substance on the probe immobilization substrate, detection 303 of the spot pattern number is read as encoded information and is inputted as a spot pattern number 304.

A spot pattern, which is allocated to the read and inputted spot pattern number 304, is selected in advance from a collection of spot patterns, which indicates an arrangement of probes in spot addresses corresponding to respective spot pattern numbers used in the spot operation, and an analysis operation 306 for specifying a spot address of the spot pattern is performed. An operation for diagnosis 309 is performed which extracts information on which target substance is included in a sample served for measurement or information on a content of the target substance in the sample from a spot address 308, in which probes of the analyzed respective probe numbers are spotted, the hybridization result 307 detected in the respective spot addresses, and product information (probe information) 311 indicating what kind of target substance the probes of the respective probe numbers specifically bind to. This extracted diagnosis information can be outputted directly or can be outputted as a diagnosis result 310 with the addition of an interpretation corresponding to this diagnosis information.

Note that it is unnecessary to incorporate the collection of spot patterns 305 in the detection device in advance. For example, it is also possible that a device, which can be used to input a collection of spot patterns, is provided in the detection device to input the collection of spot patterns at appropriate time. More specifically, it is also possible that a floppy disk reading device is provided in the detection device, and a collection of spot patterns recorded in a floppy disk in advance is inputted to a spotter from the reading device.

In addition, in the case where a method of creating spot patterns on the basis of predetermined information each time is adopted instead of the method of selecting a spot pattern from the collection of spot patterns, a type of a pseudo-random number generation algorithm to be used in the analysis device and a value of a seed thereof are detected through input or automatically, and the same spot patterns are prepared in accordance with the above-mentioned spot pattern preparation method. As described above, if the pseudo-random number generation algorithm and the value of the seed are determined, it is possible to prepare the same patterns as the spot patterns prepared by the spotter. Thus, by using this method, an operation for diagnosis is performed which extracts information on which target substance is included in a sample served for measurement or information on a content of the target substance in the sample from hybridization result detected by the detection device, and product information (probe information) indicating what kind of target substance the probes of the respective probe numbers specifically bind to. This extracted diagnosis information can be outputted directly or can be outputted as a diagnosis result with the addition of an interpretation corresponding to this diagnosis information. Note that this decoding device may be included in the detection device or the like.

The present invention is not limited to the above embodiments and various changes and modifications can be made within the spirit and scope of the present invention. Therefore to apprise the public of the scope of the present invention, the following claims are made.

What is claimed is:

1. A detection device that detects in which one of plural spot portions each of plural probes in a probe immobilization substrate is spotted, wherein the probe immobilization substrate is formed by immobilizing the plural probes, wherein the plural probes are capable of specifically binding to a target substance, in the plural spot portions on a solid phase substrate, and wherein the plural spot portions are arranged in a spot position pattern that is encrypted, the detection device comprising:

means for acquiring key information for decoding the encrypted spot position pattern of each probe immobilization substrate which is an object of detection;

means for acquiring seed information for decoding the encrypted spot position pattern;

means for decoding the encrypted spot position pattern based on the key information and the seed information; and means for identifying each of the plural probes immobilized in the plural spot portions on each probe immobilization substrate according to the decoded spot position pattern.

2. A detection device according to claim 1, wherein the spotting of the plural probes onto the solid phase substrate in the probe immobilization substrate is arranged in accordance with one spot position pattern selected out of predetermined plural spot position patterns that are applicable to the probe immobilization substrate, wherein a pattern number, which is affixed to the selected spot position pattern in advance, is marked on the solid phase substrate or in a housing to be annexed to the solid phase substrate, wherein the means for acquiring key information comprises means for reading the marked pattern number, and wherein the detection device further comprises:

means for specifying a spot position pattern selected for the probe immobilization substrate based on the read pattern number and on a group of pattern numbers that are affixed to respective plural spot position patterns in advance.

3. A detection device according to claim 1, wherein the spotting of the plural probes onto the solid phase substrate in the probe immobilization substrate is arranged in accordance with a spot position pattern that is created anew by applying encryption processing to a reference spot position pattern with predetermined information as a key, wherein a key for canceling the encryption processing is marked on the solid phase substrate or in a housing to be annexed to the solid phase substrate, wherein the means for acquiring key information comprises means for reading the key for canceling the encryption processing; and wherein the detection device further comprises:

means for specifying a spot position pattern created for the probe immobilization substrate by canceling the applied encryption processing in a course of creating the new spot position pattern based on the read key for canceling the encryption processing.

4. A gene diagnosis system constructed to use a probe immobilization substrate formed by immobilizing plural probes, which are capable of specifically binding to a target substance, in plural spot portions on a solid phase substrate, wherein the gene diagnosis system is further constructed to allow the target substance in a specimen to bind to the probes, which are capable of specifically binding to the target substance on the probe immobilization substrate, and wherein the gene diagnosis system further comprises the detection device according to claim 1 for detection of the target substance bound to the probes.

* * * * *